US010542985B2

(12) United States Patent
Zhan et al.

(10) Patent No.: US 10,542,985 B2
(45) Date of Patent: Jan. 28, 2020

(54) SURGICAL STAPLING DEVICE WITH FIRING INDICATOR

(71) Applicant: Covidien LP, Mansfield, MA (US)

(72) Inventors: Hui Zhan, Shanghai (CN); Junyu Zhou, Shanghai (CN); Shengwang Zhou, Shanghai (CN)

(73) Assignee: Covidien LP, Mansfield, MA (US)

( * ) Notice: Subject to any disclaimer, the term of this patent is extended or adjusted under 35 U.S.C. 154(b) by 296 days.

(21) Appl. No.: 15/531,844

(22) PCT Filed: Dec. 17, 2014

(86) PCT No.: PCT/CN2014/094007
§ 371 (c)(1),
(2) Date: May 31, 2017

(87) PCT Pub. No.: WO2016/095112
PCT Pub. Date: Jun. 23, 2016

(65) Prior Publication Data
US 2017/0319206 A1    Nov. 9, 2017

(51) Int. Cl.
*A61B 17/072* (2006.01)
*A61B 17/115* (2006.01)
*A61B 90/00* (2016.01)

(52) U.S. Cl.
CPC .... *A61B 17/07207* (2013.01); *A61B 17/1155* (2013.01); *A61B 2017/07257* (2013.01); *A61B 2017/07278* (2013.01); *A61B 2090/0811* (2016.02)

(58) Field of Classification Search
CPC .......... A61B 17/07207; A61B 17/1155; A61B 17/105

USPC .......................... 227/177.1, 176.1, 175.1, 19
See application file for complete search history.

(56) References Cited

U.S. PATENT DOCUMENTS

| | | | |
|---|---|---|---|
| 3,193,165 | A | 7/1965 | Akhalaya et al. |
| 3,388,847 | A | 6/1968 | Kasulin et al. |
| 3,552,626 | A | 1/1971 | Astafiev et al. |
| 3,638,652 | A | 2/1972 | Kelley |
| 3,771,526 | A | 11/1973 | Rudie |
| 4,198,982 | A | 4/1980 | Fortner et al. |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

International Search Report for PCT/CN14/094007 date of completion is Aug. 14, 2015 (2 pages).

(Continued)

*Primary Examiner* — Nathaniel C Chukwurah

(57) ABSTRACT

A surgical stapling device (10) having an indicator mechanism that is movable between first, second and third positions. The first position of the indicator (26) indicates to a clinician that the jaws of the surgical stapling device (10) have yet to be approximated. The second position of the indicator (26) indicates to a clinician that the jaws of the surgical stapling device (10) are approximated. The third position of the indicator (26) indicates to a clinician that the surgical stapling device (10) has been fired and is depleted of staples.

16 Claims, 10 Drawing Sheets

(56) References Cited

U.S. PATENT DOCUMENTS

| | | |
|---|---|---|
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |

(56) References Cited

U.S. PATENT DOCUMENTS

| | | |
|---|---|---|
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |

(56) References Cited

U.S. PATENT DOCUMENTS

| | | |
|---|---|---|
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2005/0116009 A1* | 6/2005 | Milliman ............. A61B 17/068 227/176.1 |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0173767 A1 | 7/2009 | Milliman |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0108741 A1* | 5/2010 | Hessler ............... A61B 17/1114 227/179.1 |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |

(56) References Cited

U.S. PATENT DOCUMENTS

| | | |
|---|---|---|
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |

FOREIGN PATENT DOCUMENTS

| | | |
|---|---|---|
| CN | 103462663 A | 12/2013 |
| CN | 203379170 U | 1/2014 |
| CN | 104042288 A | 9/2014 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2009213893 A | 9/2009 |
| JP | 2011025029 A | 2/2011 |
| JP | 2013-138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 2001/054594 A1 | 8/2001 |
| WO | 2008/107918 A1 | 9/2008 |

OTHER PUBLICATIONS

Japanese Office Action dated Aug. 23, 2018, issued in JP Appln. No. 2017532095.

* cited by examiner

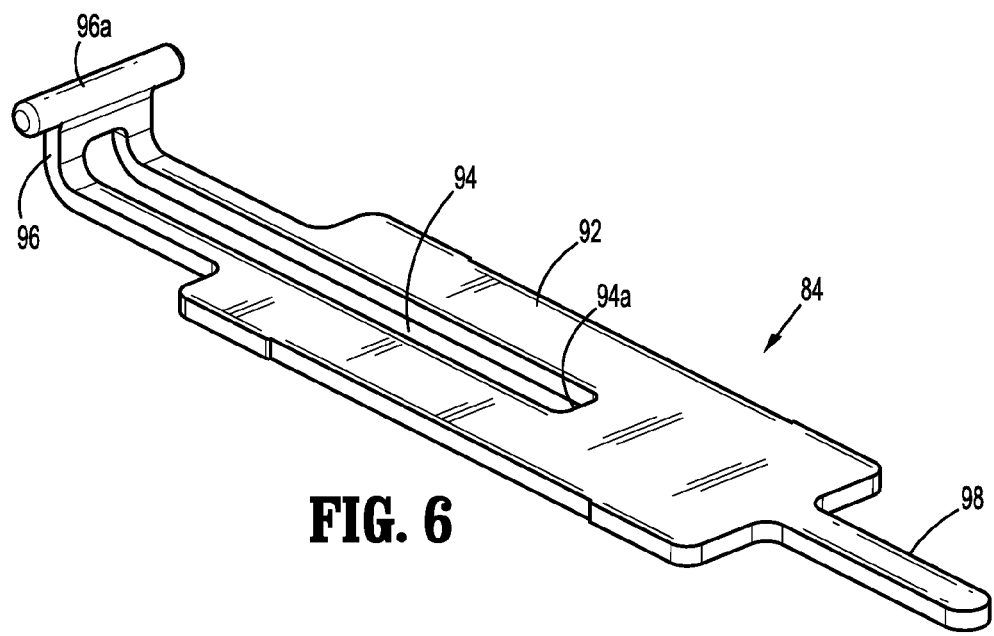
FIG. 6
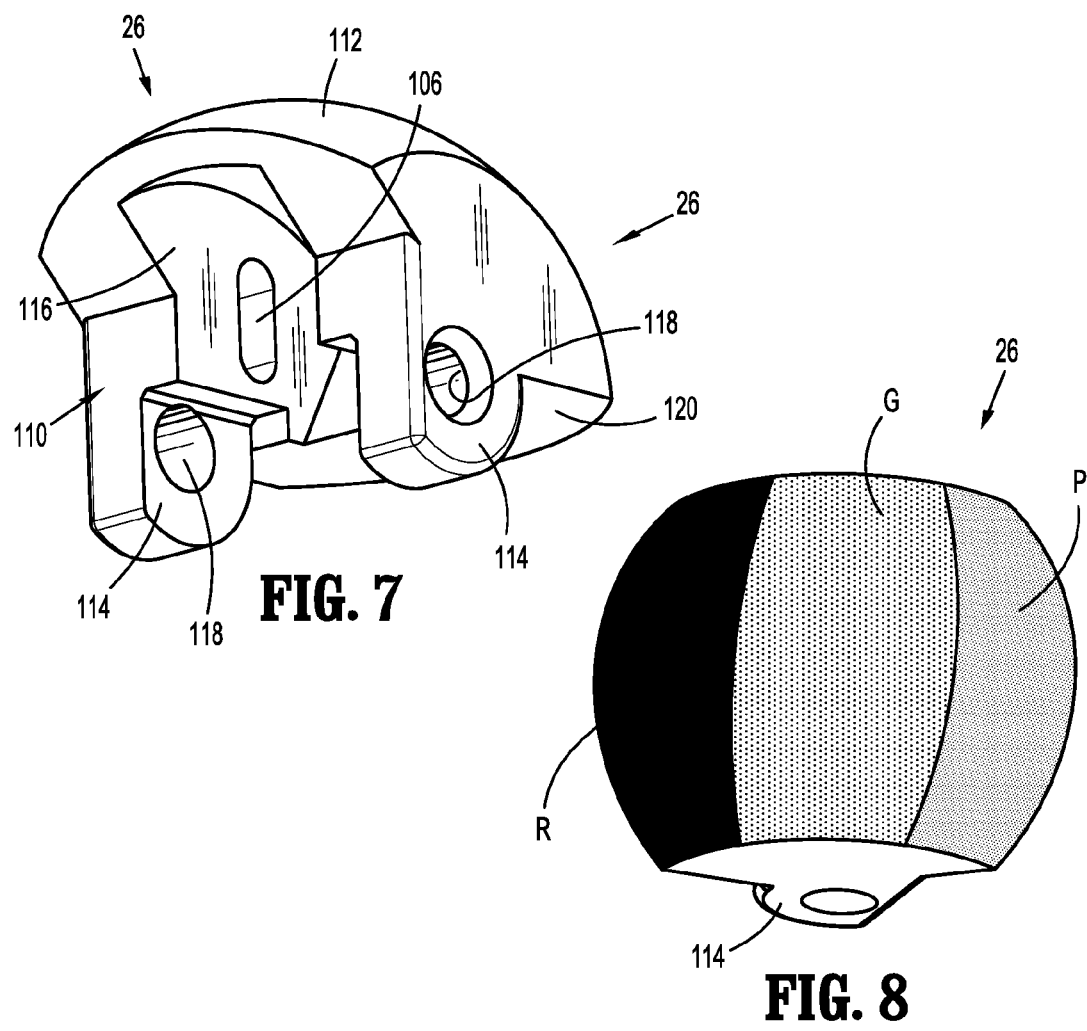
FIG. 7
FIG. 8

SURGICAL STAPLING DEVICE WITH FIRING INDICATOR

CROSS-REFERENCE TO RELATED APPLICATIONS

This application is a National Stage Application of PCT/CN2014/094007 under 35 USC § 371(a), the disclosure of the above-identified application is hereby incorporated by reference in its entirety

BACKGROUND

1. Technical Field

The present disclosure relates to surgical stapling devices and, more particularly, to surgical stapling devices that include a firing indicator for providing an indication to a clinician that the stapling device has been fired.

2. Background of Related Art

Surgical stapling devices having an end effector configured to clamp and suture tissue are well known in the medical arts. Typically, these devices include a handle assembly having a firing trigger, a body portion, and a tool assembly supported on the distal end of the body portion. The tool assembly includes a first jaw which supports an anvil assembly and a second jaw which supports a cartridge assembly which houses a plurality of staples. In use, the first and second jaws are movable in relation to each other between spaced and approximated positions to clamp tissue between the jaws. After the tissue has been clamped between the jaws, the firing trigger is actuable to fire the staples from the cartridge assembly through the tissue into the anvil assembly.

In some embodiments, an indicator is provided on the handle assembly of the surgical stapling device to identify to a clinician when the device is in a fire-ready position, i.e., a position in which the anvil assembly and the cartridge assembly are approximated sufficiently to allow for the proper formation of staples from the cartridge assembly against the anvil assembly.

In known stapling devices, after the firing trigger has been actuated and the staples have been ejected from the cartridge, there is nothing on the device that indicates to a clinician that the surgical stapling device has been fired and is depleted of staples. Operation of the surgical stapling device by a clinician who is unaware that the surgical stapling device is depleted of staples could result in serious injury to a patient.

A need exists in the art of surgical stapling devices for a simple, inexpensive device for identifying to a clinician that the surgical stapling device has been fired.

SUMMARY

One aspect of the present disclosure is directed to a surgical stapling device that includes a handle assembly including a housing defining a window, a firing trigger supported on the housing, and an indicator mechanism. The firing trigger is actuable to fire the stapling device. A body extends distally from the handle assembly and a shell assembly is supported on a distal end of the body. An approximation assembly extends from the handle assembly through the body and includes an approximation knob supported on the handle assembly. An anvil assembly is supported on a distal end of the approximation assembly. The approximation assembly is actuable to move the anvil from an unapproximated position spaced from the shell assembly to an approximated position adjacent the shell assembly. The indicator mechanism includes an indicator that is pivotally supported within the housing adjacent the window, a slide plate and an indicator link. The slide plate is operably associated with the indicator and is movable within the housing to move the indicator from a first position to a second position in response to movement of the anvil assembly from the unapproximated position to the approximated position. The indicator link is positioned within the housing and is operably associated with the indicator and movable in response to actuation of the firing trigger to move the indicator from the second position to a third position.

In embodiments, the firing trigger is pivotally supported on the housing.

In some embodiments, the stapling device includes a firing link having a first end pivotally connected to the firing trigger and a second end pivotally connected to the housing.

In certain embodiments, the firing link includes a lateral extension positioned to engage the indicator link to move the indicator link within the housing to effect movement of the indicator from the second position to the third position.

In embodiments, the indicator link is slidable within a slot defined along an inner wall of the housing.

In some embodiments, the indicator link includes a central body portion, an upper portion and a lower portion. The lower portion is positioned to engage the lateral extension of the firing link and the upper portion is positioned to engage the indicator.

In certain embodiments, the indicator includes an abutment surface that is positioned to engage the upper portion of the indicator link.

In embodiments, the slide member includes a cylindrical connector and the indicator includes at least one recess. The cylindrical connector is received within the at least one recess to connect the slide member to the indicator.

In some embodiments, the cylindrical connector is formed on an upturned lip portion of the slide member.

In certain embodiments, the indicator includes a body having a top surface including indicia to identify each of the three positions of the indicator.

In embodiments, the indicia include three different colors positioned on the top surface of the body of the indicator.

In some embodiments, a biasing member is positioned to urge the slide member to a position to maintain the indicator in the first position.

In certain embodiments, the slide member includes a body portion defining an elongated slot, an upturned lip portion supporting a connector, and a proximal extension.

In embodiments, the biasing member is positioned about the proximal extension of the body of the slide member and is compressed between the housing of the handle assembly and the body of the slide member.

In some embodiments, the approximation mechanism includes a drive screw supporting a screw stop having a protrusion positioned within the elongated slot of the slide member wherein movement of the drive screw to move the anvil assembly to the approximated position effects movement of the protrusion through the elongated slot into contact with the slide member such that contact of the protrusion with the slide member effects movement of the slide member to pivot the indicator from the first position to the second position.

In some embodiments, the indicator mechanism includes a lens cover defining a slot. The lens cover is positioned over the indicator such that the indicia is visible through the slot.

BRIEF DESCRIPTION OF THE DRAWINGS

Various embodiments of the presently disclosed surgical stapling device and firing indicator are described herein with reference to the drawings, wherein:

FIG. 6 is a perspective view of an indicator plate of an indicator assembly of the surgical stapling device of FIG. 4;

FIG. 7 is a side perspective view of an indicator member of the indicator assembly shown in FIG. 4;

FIG. 8 is a top perspective view of the indicator member shown in FIG. 7;

DETAILED DESCRIPTION OF EMBODIMENTS

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

As used herein, the term distal refers to that portion of the device which is farthest from the clinician, while the term proximal refers to that portion of the device which is closest to the clinician. In addition, as used herein, the term clinician refers to medical staff including doctors, nurses and support personnel.

The presently disclosed surgical stapling device includes a pivotal indicator supported on a handle assembly of the surgical stapling device. The indicator is pivotal from a first position to a second position in response to movement of the surgical stapling device from an unapproximated position to an approximated position to indicate to a clinician that the stapling device is in a fire-ready position. The surgical stapling device further includes an indicator link which is positioned to engage and move the indicator from the second position to a third position in response to actuation of a firing trigger of the surgical stapling device to indicate to a clinician that the surgical stapling device has been fired. The surgical stapling device will be described in detail below.

Figure 1:
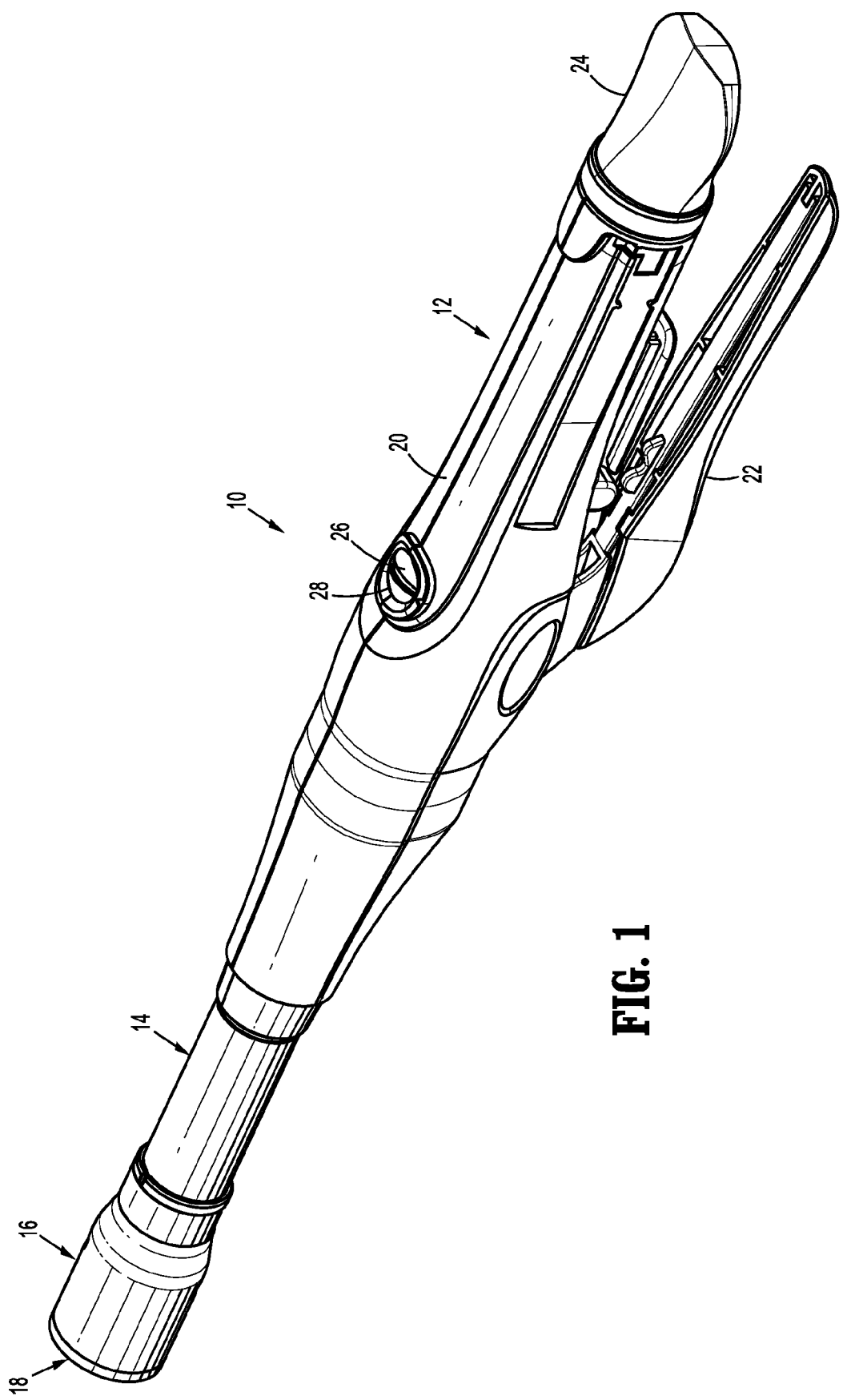
FIG. 1 is a side perspective view of one embodiment of the presently disclosed surgical stapling device with an end effector in an approximated position and a firing trigger actuated.

FIG. 1 illustrates one embodiment of the presently disclosed surgical stapling device shown generally as 10. Surgical stapling device 10 includes a handle assembly 12, a body 14 that extends distally from the handle assembly 12, a cartridge or shell assembly 16 supported on a distal end of the body 14, and an anvil assembly 18 that is movably supported in relation to the shell assembly 16 between a position spaced from the shell assembly 16 to a position in juxtaposed alignment with the shell assembly 16. The handle assembly 12 includes a housing 20, a firing trigger 22 pivotally supported on the housing 20, an approximation knob 24 rotatably supported on the housing 20, and an indicator 26 which is visible through a window 28 formed through an upper wall of the housing 20. As illustrated, the indicator 26 may have a bulbous or convex shape such that the indicator 26 protrudes through the window 28. The bulbous shape of the indicator 26 allows visualization of the indicator 26 from opposite sides of the stapling device 10. U.S. Pat. No. 7,303,106 ("the '106 patent") discloses a surgical stapling device that includes many of the same components and mechanisms described in further detail and is incorporated herein by reference in its entirety.

Figure 2:
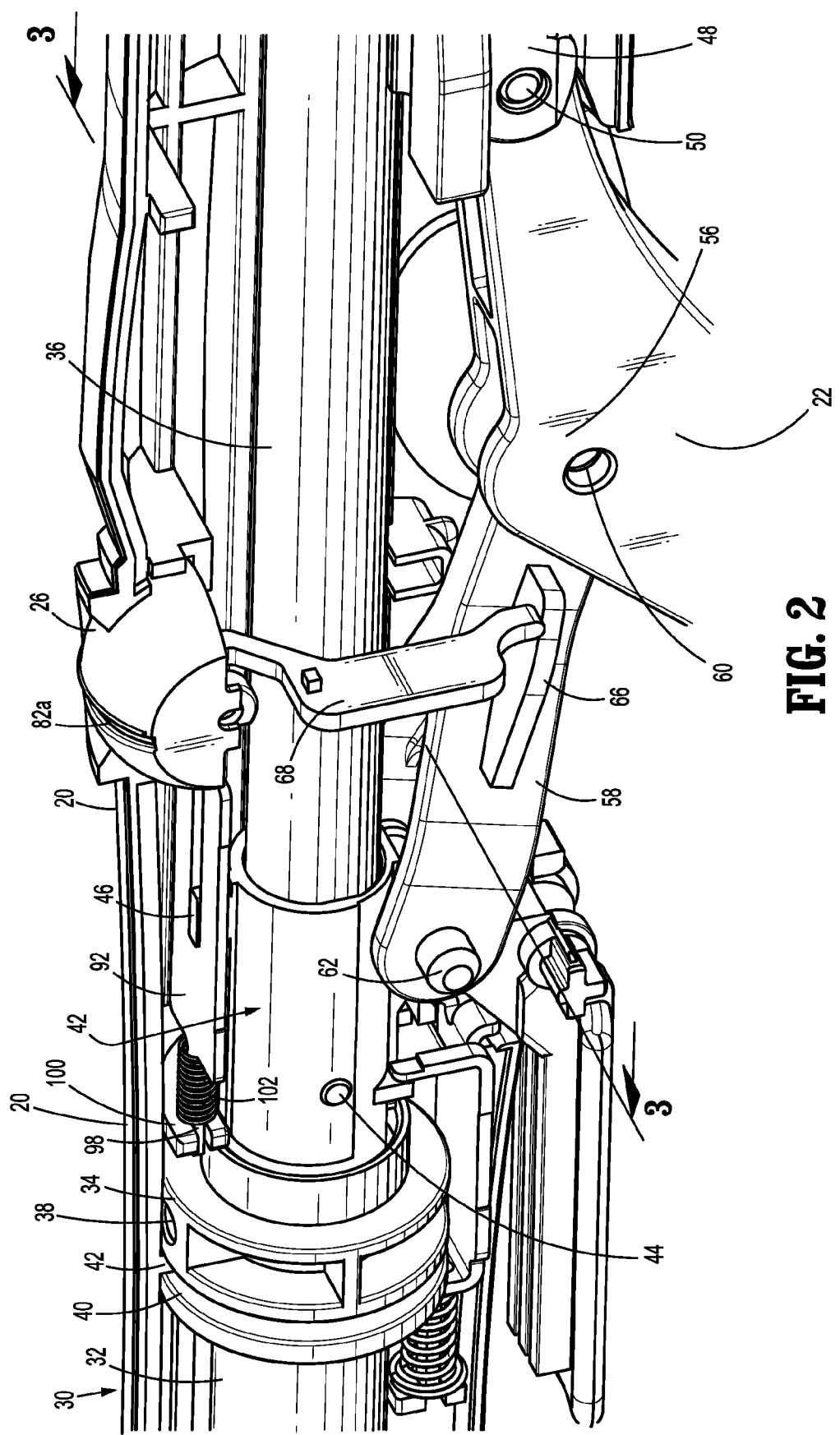
FIG. 2 is a side perspective view of a handle assembly of the surgical stapling device shown in FIG. 1 with a body half removed and the firing trigger in a non-actuated position.
Figure 3:
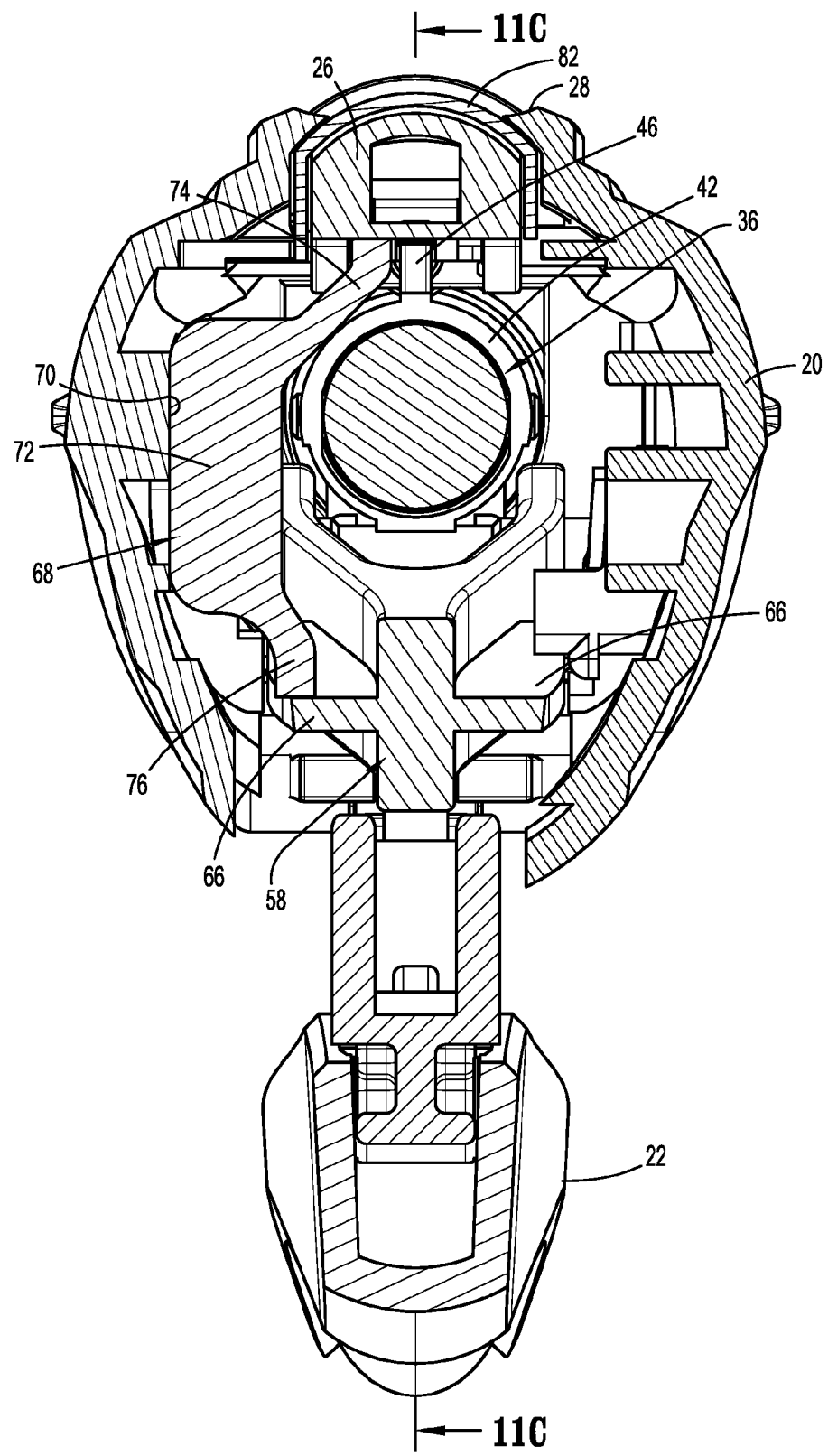
FIG. 3 is a cross-sectional view taken along section line 3-3 of FIG. 2.

Referring also to FIG. 2, the handle assembly 12 supports an approximation assembly 30. The approximation assembly 30 includes the approximation knob 24 (FIG. 1), a hollow sleeve 32, a collar 34 fixedly secured to one end of the hollow sleeve 32, and a drive screw 36. The drive screw 36 has a proximal end that extends through the collar 34 and into the hollow sleeve 32 and a distal end that is operably connected to the anvil assembly 18. The drive screw 32 includes a helical groove (not shown) that receives a pin 38 supported on the collar 34.

The approximation knob 24 (FIG. 1), sleeve 32, and collar 34 are rotatably supported on the proximal end of the housing 20 of the handle assembly 12 with the pin 38 received within the helical groove. The collar 34 defines an annular groove 40 that receives a flange 42 formed on the inner wall of the housing 20 to axially fix the collar 34 within the housing 20. As such, when the approximation knob 24 is actuated or rotated in relation to the proximal end of the housing 20, the pin 38 moves within the helical groove (not shown) of the drive screw 36 to effect linear movement of the drive screw 36 into and out of the hollow sleeve 32. The '106 patent which has been incorporated herein by reference discloses an approximation assembly substantially similar to approximation assembly 30.

A screw stop 42 is axially fixed to the drive screw 36 using, for example, a set screw 44. The screw stop 42 includes an upwardly directed protrusion 46 which will be discussed in further detail below. When the approximation knob 24 is actuated and the drive screw 36 is moved linearly within the housing 20 of the handle assembly 12, the screw stop 42 including the protrusion 46 are also moved linearly within the housing 20.

Figure 4:
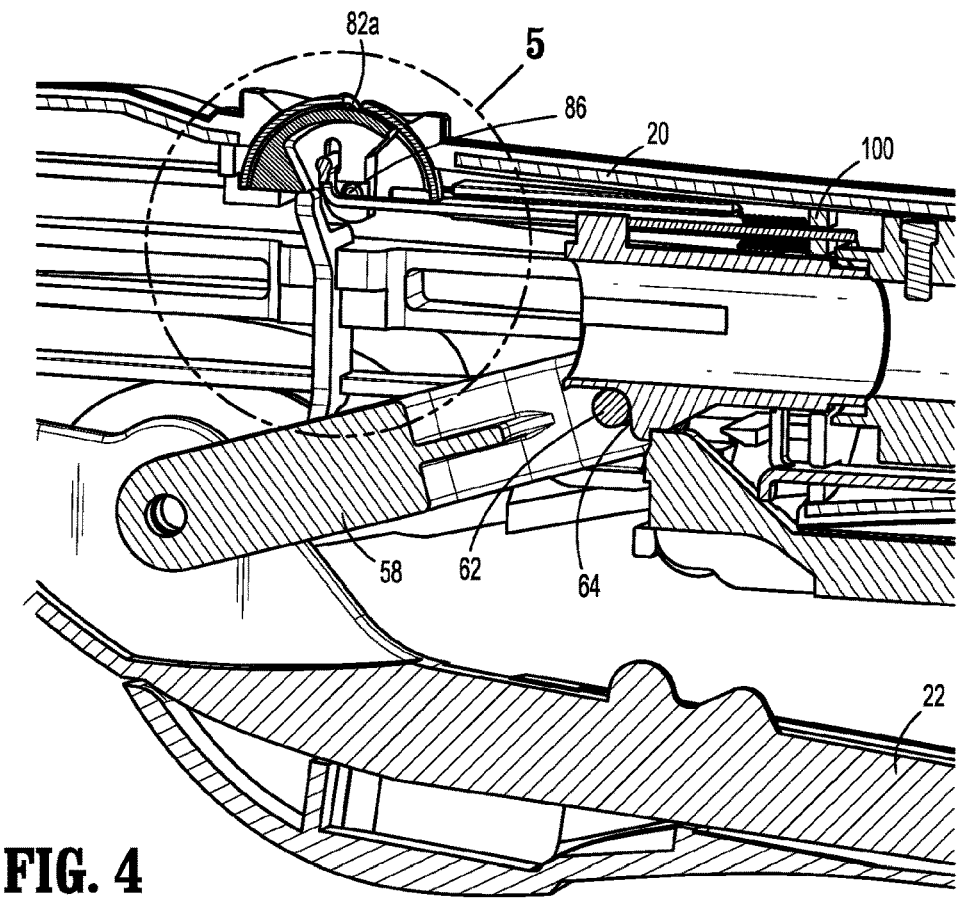
FIG. 4 is a side cross-sectional view through a portion of the handle assembly with the firing trigger in an actuated position.
Figure 5:
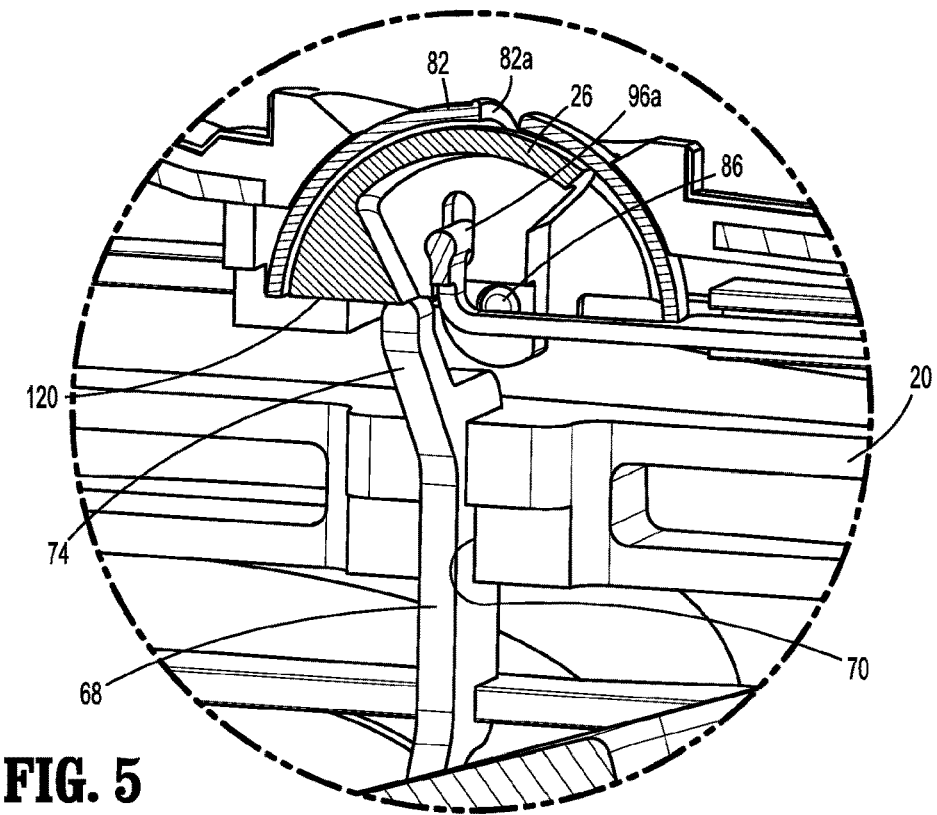
FIG. 5 is an enlarged view of the indicated area of detail shown in FIG. 4.

The firing trigger 22 is pivotally coupled to a proximal end of a pusher link 48 by a pivot pin 50. As is known in the art, the pusher link 48 engages a pusher (not shown) positioned in the shell assembly 16 (FIG. 1) to eject staples from the shell assembly 16 when the firing trigger 22 is actuated as will be discussed in further detail below. A central portion 56 of the firing trigger 22 is pivotally coupled to a distal end of a firing link 58 by a pivot member 60. A proximal end of the firing link 58 supports a drive pin 62 that is positioned to engage a backstop 64 (FIG. 4) formed on the screw stop 42 when the firing trigger 22 is actuated. More specifically, when the firing trigger 22 is actuated, i.e., compressed towards the housing 20 of the handle assembly 12, the drive pin 62 engages the backstop 64 of the screw stop 42 and the distal end of the firing link 58 is pivoted towards the housing 20 to advance the pusher link 48 distally.

Figure 9:
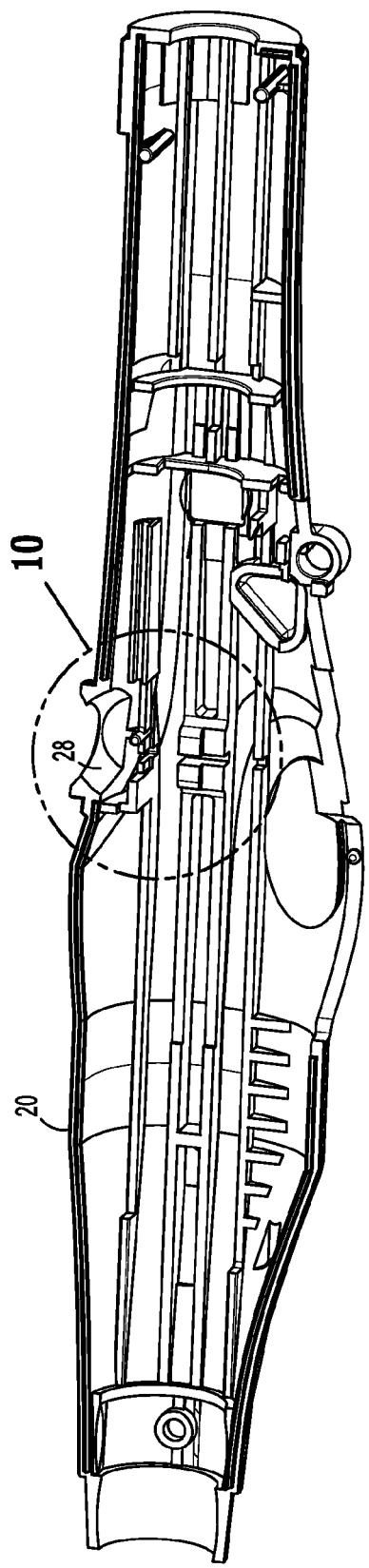
FIG. 9 is a side perspective view of an inner surface of a body half of the handle assembly of the surgical stapling device shown in FIG. 1.

Referring to FIGS. 2-5, the firing link 58 includes a lateral extension 66. An indicator link 68 is slidably positioned within a slot 70 (FIGS. 9 and 10) defined within an inner wall of the housing 20. The indicator link 68 includes a central body portion 72, an upper portion 74 and a lower portion 76. The central body portion 72 is slidably received in the slot 70 within the housing 20 such that the upper portion 74 is positioned to engage a bottom surface of the indicator 26 and the lower portion 76 is positioned to engage the lateral extension 66 of the firing link 58 when the firing trigger 22 is actuated.

Referring also to FIGS. 6-10, the presently disclosed surgical stapling device 10 includes an indicator mechanism that includes the indicator 26, a lens cover 82 (FIG. 5) and a slide member 84 (FIG. 6). The indicator 26 is pivotally supported about a pivot member 86 which can be integrally formed on the inner wall of the housing 20. Alternatively, the pivot member 86 can be formed separately from the housing 20. The lens cover 82 is positioned above indicator 26 and defines a slot 82a through which the indicator 26 can be visualized. The slide member 84 (FIG. 6) includes a body portion 92 having a elongated slot 94 formed therein, a distal abutment member or upturned lip portion 96, and a proximal extension 98. The slide member 84 is slidably positioned within the housing 20. Proximal extension 98 is slidably supported within the housing 20 by a support structure 100 (FIG. 2) which may be integrally formed with the housing 20. A biasing member, e.g., a coil spring 102, is positioned in compression about proximal extension 98 between support structure 100 and body portion 92 of slide member 84 to urge slide member 84 distally within the housing 20.

Referring also to FIGS. 7 and 8, an upper end of the lip portion 96 includes a cylindrical connector 96a. The indicator 26 includes a pair of spaced elongated recesses 106 (FIG. 9, only one recess is shown) which receive opposite ends of the cylindrical connector 96a. In the unapproximated position of stapling device 10, the biasing member 102 (FIG. 2) urges slide member 84 to its distal most position to pivot the indicator 26 to a first position which provides an indication to a clinician that the stapling device 10 has not been approximated and is not in a fire-ready condition as will be discussed in further detail below.

As discussed above, the screw stop 42 is fixedly attached to the drive screw 42 (FIG. 2) and includes a protrusion 46. The protrusion 46 is positioned to travel through slot 94 of the slide member 84 and engage a proximal end 94a (FIG. 6) of slot 94 during approximation of the stapling device 10. When protrusion 46 of the screw stop 42 abuts proximal end 94a of the slot 94a, further approximation of the stapling device 10 moves slide plate 84 proximally within the housing 20 against the bias of the spring 102. As the slide plate 84 moves proximally within the housing 20, the cylindrical connector 96a of the slide member 84, which is positioned within the elongated recesses 106 of the indicator 26 at a position offset from the pivot member 86, effects pivotal movement of the indicator 26 about the pivot member 86 from the first position to a second position to provide an indication to a clinician that the stapling device 10 is in an approximated and fire-ready position.

Figure 10:
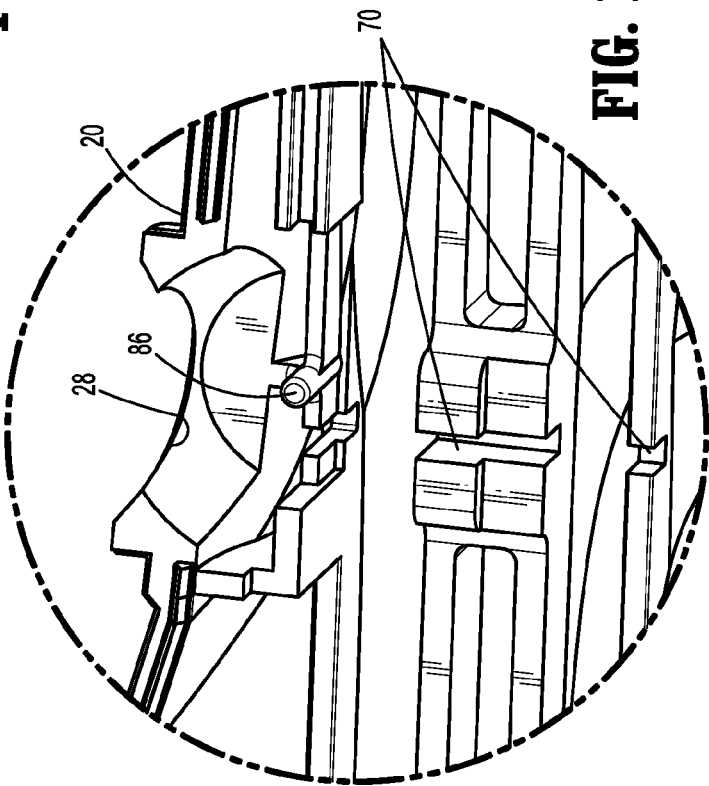
FIG. 10 is an enlarged view of the indicated area of detail shown in FIG. 9.

Referring to FIGS. 7 and 8, the indicator 26 includes a body 110 having a top surface 112, a pair of spaced hinge members 114, and an inner surface 116 defining the elongated recesses 106. The hinge members 114 extend downwardly from the body 110 and define openings 118 that receive the pivot member 86 (FIG. 10). The body 110 also defines an abutment surface 120 that is positioned between the hinge members 114. The abutment surface 120 is positioned to engage the upper portion 74 of the indicator link 68 when the firing trigger 22 is actuated as discussed in further detail below. The top surface 112 of the body 110 of the indicator 26 includes indicia that indicate three different positions of the indicator 26. As discussed above, the first position of the indicator 26 provides an indication to a clinician that the stapling device is in an unapproximated position and is not fire-ready and the second position of the indicator 26 provides an indication to a clinician that the stapling device has been approximated and is in a fire-ready position. As discussed below, the indicator 26 is movable to a third position that provides an indication to a clinician that the stapling device 10 has been fired.

The indicia provided on the upper surface 112 of the indicator body 110 may include a variety of different colors or alpha numeric identifiers to distinguish or identify each of the positions of the indicator. In embodiments, the indicia includes three distinct colors, e.g., red (R), green (G) and pink (P), provided on the top surface 112 of the indicator 26. The colors R, G and P are positioned on the top surface 112 of the indicator 26 such that when the indicator 26 is positioned in its first position, the first color, e.g., R, is visible through the slot 82a (FIG. 5) in the lens cover 82, when the indicator 26 is positioned in its second position, the second color, e.g., G, is visible through the slot 82a in the lens cover 82, and when the indicator 26 is positioned in its third position, the third color, e.g., P, is visible through the slot 82a in the lens cover 82. Alternately, the colors can be replaced by a variety of different letters, numbers or symbols.

Figure 11A:
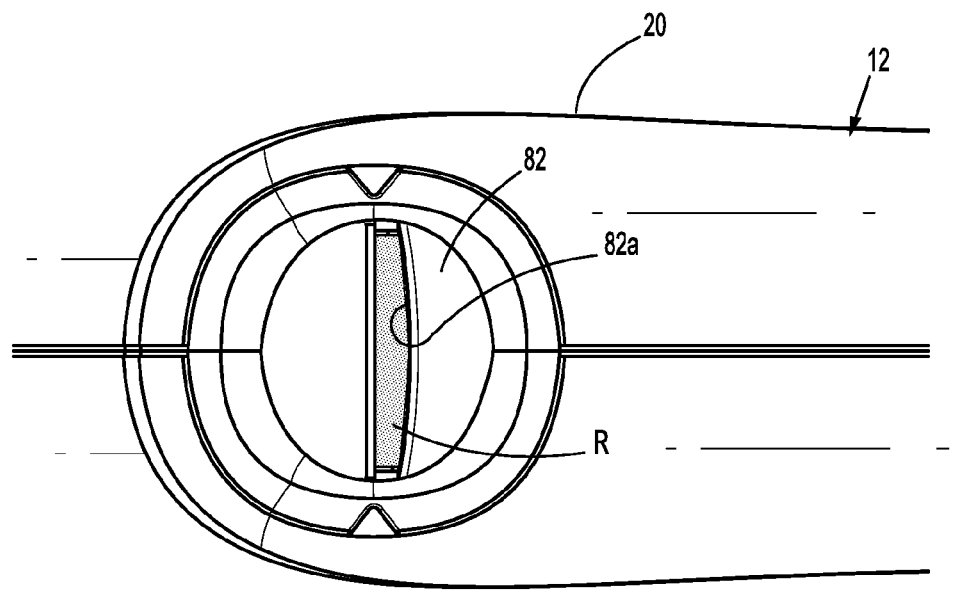
FIG. 11A is a top view of an upper surface of the handle assembly of the surgical stapling device shown in FIG. 1 illustrating the indicator assembly in a first position prior to approximation and firing of the surgical stapling device.
Figure 11B:
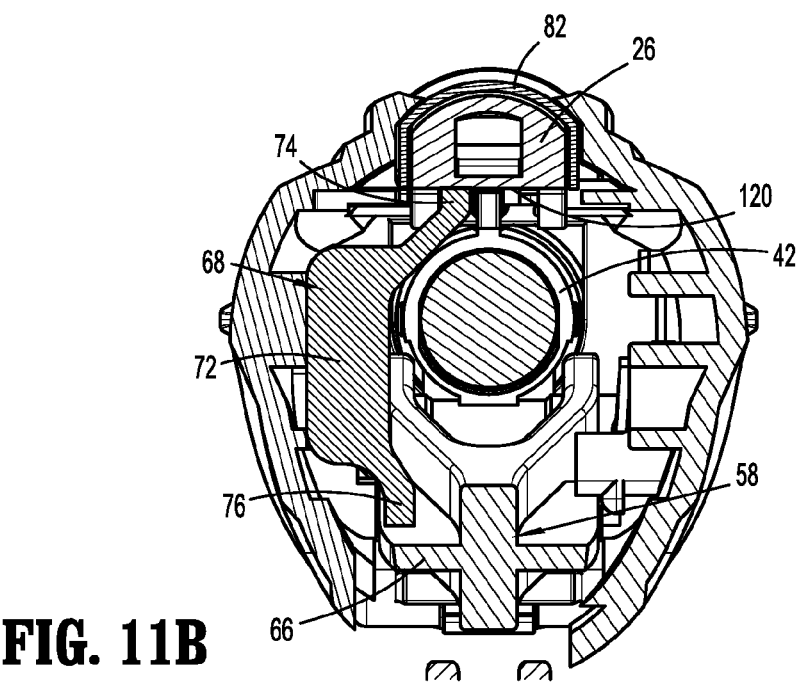
FIG. 11B is a transverse cross-sectional view through the indicator assembly of the surgical stapling device shown in FIG. 1 with the indicator assembly shown in the first position.
Figure 11C:
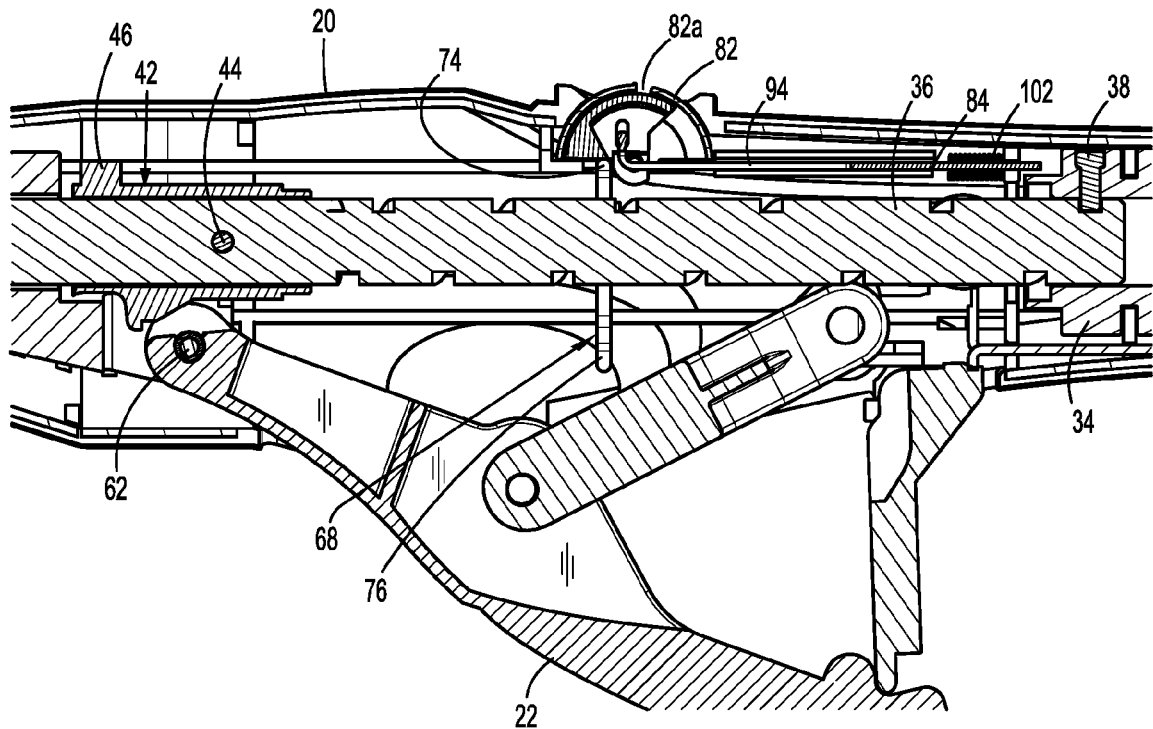
FIG. 11C is a cross-sectional view taken along section line 11C-11C of FIG. 3 with the indicator assembly in the first position.

Referring to FIGS. 11A-11C, prior to actuation of the surgical stapling device 10, (FIG. 1) with the stapling device 10 in an unapproximated position (FIG. 1A), the indicator 26 is in its first position such that the color R is visible through the slot 82a in the lens cover 82. In addition, the upper portion 74 of the indicator link 68 is positioned adjacent the abutment surface 120 of the indicator body 110 and the lower portion 76 is spaced from the lateral extension 66 of the firing link 58. As shown, the screw stop 42 is spaced distally of the collar 34 of the approximation mechanism and the slide member 84 is in its distal-most position with the biasing member or spring 102 in an uncompressed condition. As shown, the protrusion 46 of the screw stop 42 is positioned in the distal end of the elongated slot 94 of the slide member 84.

Figure 11D:
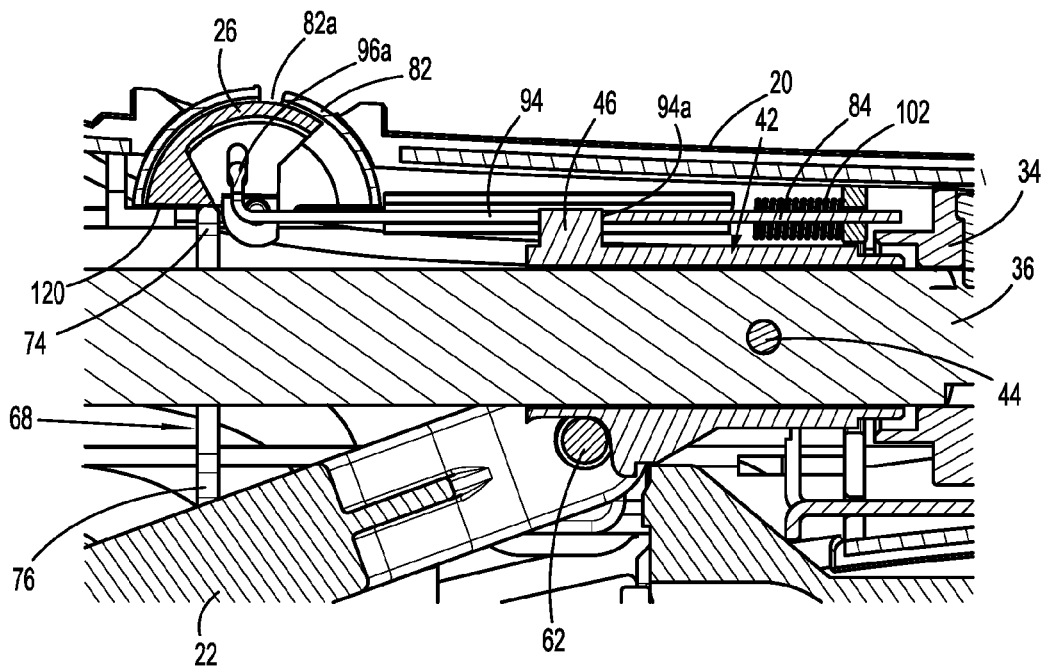
FIG. 11D is a cross-sectional view along the section line 11C-11C of FIG. 3 with the device in a partially approximated position.

FIG. 11D illustrates the stapling device 10 in a partially approximated position in which the stapling device 10 has been approximated to move the anvil assembly 18 towards the cartridge assembly 16 by actuating the approximation knob 24 (FIG. 1). In the partially approximated position shown, the screw stop 42, which is positioned distally of the collar 34, has moved proximally with the drive screw 36 towards the collar 34 such that the protrusion 46 of the drive screw 36 has moved from a distal end of the slot 94 to a position adjacent the proximal end 94a of the slot 94. As illustrated, the stapling device 10 is not in the fully approximated position. As such, the protrusion 46 of the screw stop 42 has yet to move the slide member 84 proximally within the housing 20 and, as such, the slide member 84 is still in its distal-most position.

Figure 12A:
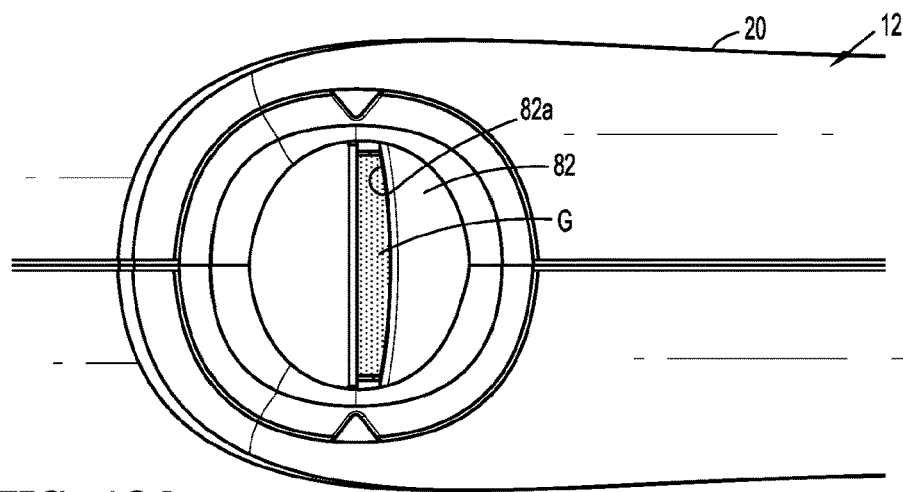
FIG. 12A is a top view of an upper surface of the handle assembly of the surgical stapling device shown in FIG. 1 illustrating the indicator assembly in a second position after approximation but prior to firing of the surgical stapling device.
Figure 12B:
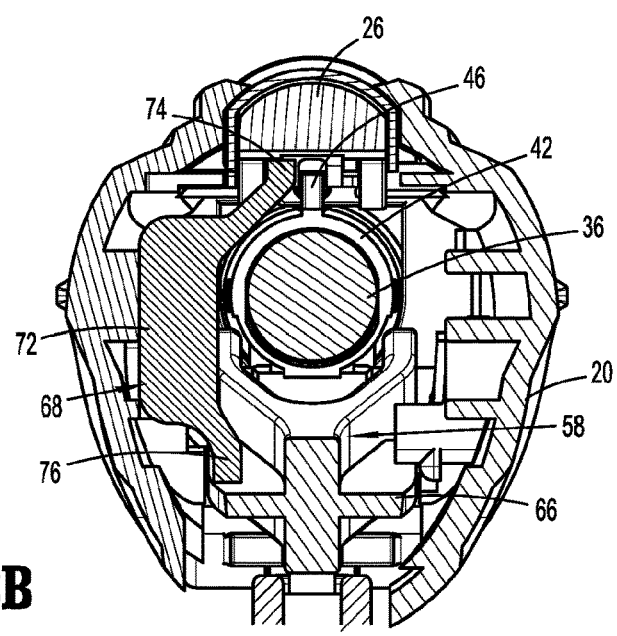
FIG. 12B is a transverse cross-sectional view through the indicator assembly of the surgical stapling device shown in FIG. 1 with the indicator assembly shown in the second position.
Figure 12C:
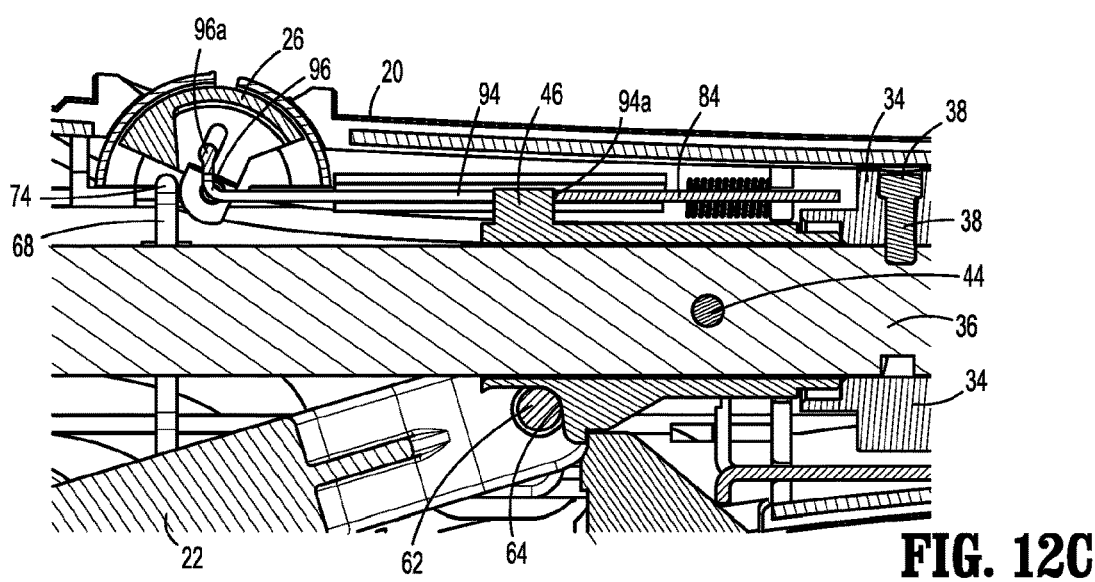
FIG. 12C is a cross-sectional view taken along section line 11C-11C of FIG. 3 with the indicator assembly in the second position.

Referring to FIGS. 12A-12C, when the stapling device 10 (FIG. 1) is moved from the partially approximated position shown in 11D to the fully approximated position to move the anvil assembly 18 into juxtaposed alignment with the cartridge assembly 16, the protrusion 46 of the screw stop 42 engages the slide member 84 at the proximal end 94a (FIG. 12C) of the slot 94 and retracts the slide member 84 within the housing 20. As the slide member 84 moves proximally within the housing 20, the slide member 84, which is connected to the indicator 26 via the cylindrical connector 96a of lip portion 96 of the slide member 84, causes the indicator 26 to pivot in a clockwise direction, as viewed in FIG. 12C, from its first position to its second position. As discussed above, in the second position of the indicator 26, the second color, e.g., G, is visible through the slot 82a in the lens cover 82 to provide an indication to a clinician that the stapling device 10 is in the approximated position. It is noted that in the fully retracted position of the drive screw 36, the screw stop 42 is in engagement with the collar 34 (FIG. 12C).

Figure 13A:
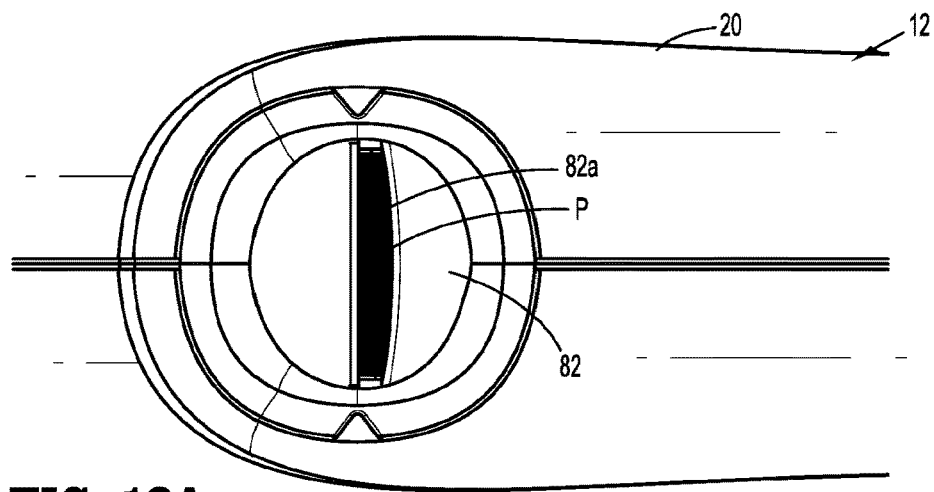
FIG. 13A is a top view of an upper surface of the handle assembly of the surgical stapling device shown in FIG. 1 illustrating the indicator assembly in a third position after approximation and firing of the surgical stapling device.
Figure 13B:
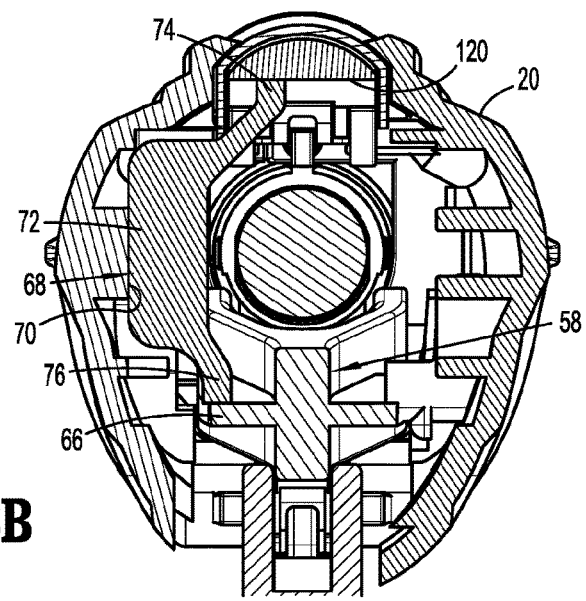
FIG. 13B is a transverse cross-sectional view through the indicator assembly of the surgical stapling device shown in FIG. 1 with the indicator assembly shown in the third position.
Figure 13C:
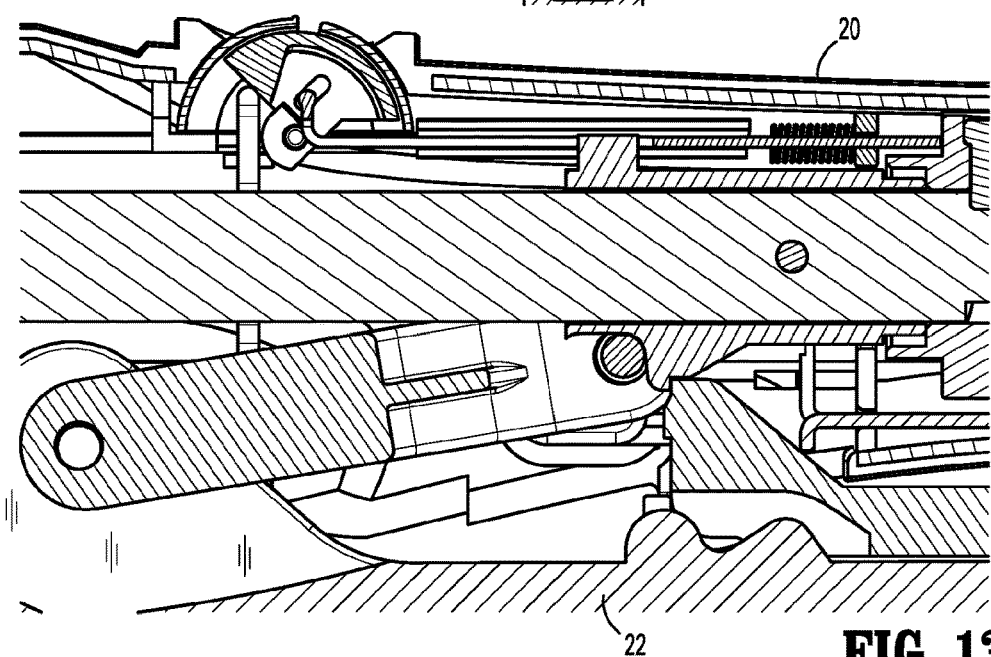
FIG. 13C is a cross-sectional view taken along section line 11C-11C of FIG. 3 with the indicator assembly in the third position.

Referring to FIGS. 13A-13C, after the stapling device has been moved to the fully approximated position, the stapling device can be fired to eject staples from the cartridge assembly 16. Stapling device 10 is fired by pivoting the firing trigger 22 towards the housing 20 of the handle assembly 12. As discussed above, as the firing trigger 22 is pivoted towards the housing 20 of the handle assembly 12, the firing link 58 is pivoted towards the housing 20 such that the lateral extension 66 formed on at least one side of the firing link 58 engages the lower portion 76 of the indicator link 68 to move the indicator link 68 upwardly within the slot 70 within the housing 20 of the handle assembly 12. As the indicator link 68 moves upwardly within the slot 70, the upper portion 74 of the indicator link 68 presses against the abutment surface 120 of the indicator 26 to pivot the indicator 26 from its second position to its third position. In the third position, the third color, e.g., P is visible through the slot 82a in the lens cover 82 to provide an indication to a clinician that the stapling device 10 has been fired.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical stapling device comprising:
   a handle assembly including a housing defining a window, a firing trigger supported on the housing, and an indicator mechanism, the firing trigger being actuable to fire the stapling device;
   a body extending distally from the handle assembly;
   a shell assembly supported on a distal end of the body;
   an approximation assembly extending from the handle assembly through the body, the approximation assembly including an approximation knob supported on the handle assembly; and
   an anvil assembly supported on a distal end of the approximation assembly, wherein the approximation assembly is actuable to move the anvil from an unapproximated position spaced from the shell assembly to an approximated position adjacent the shell assembly;
   wherein the indicator mechanism includes:
   an indicator pivotally supported within the housing adjacent the window;
   a slide plate operably associated with the indicator, the slide plate being movable within the housing to move the indicator from a first position to a second position in response to movement of the anvil assembly from the unapproximated position to the approximated position; and
   an indicator link positioned within the housing, the indicator link being operably associated with the indicator and being movable in response to actuation of the firing trigger to move the indicator from the second position to a third position, wherein in the third position, the indicator provides an indication that the surgical stapling device has been fired.

2. The surgical stapling device of claim 1, wherein the firing trigger is pivotally supported on the housing.

3. The surgical stapling device of claim 2, further including a firing link having a first end pivotally connected to the firing trigger and a second end pivotally connected to the housing.

4. The surgical stapling device of claim 3, wherein the firing link includes a lateral extension, the lateral extension being positioned to engage the indicator link to move the indicator link within the housing to effect movement of the indicator from the second position to the third position.

5. The surgical stapling device of claim 4, wherein the indicator link is slidable within a slot defined along an inner wall of the housing.

6. The surgical stapling device of claim 5, wherein the indicator link includes a central body portion, an upper portion and a lower portion, wherein the lower portion is positioned to engage the lateral extension of the firing link and the upper portion is positioned to engage the indicator.

7. The surgical stapling device of claim 6, wherein the indicator includes an abutment surface, the abutment surface being positioned to engage the upper portion of the indicator link.

8. The surgical stapling device of claim 1, wherein the slide member includes a cylindrical connector and the indicator includes at least one elongated recess, the cylindrical connector being received within the at least one elongated recess to connect the slide member to the indicator.

9. The surgical stapling device of claim 8, wherein the cylindrical connector is formed on an upturned lip portion of the slide member.

10. The surgical stapling device of claim 1, wherein the indicator includes a body having a top surface including indicia, the indicia being provided to identify each of the three positions of the indicator.

11. The surgical stapling device of claim 10, wherein the indicia includes three different colors positioned on the top surface of the top surface of the body of the indicator.

12. The surgical stapling device of claim 10, further including a lens cover defining a slot, the lens cover being positioned over the indicator such that the indicia is visible through the slot.

13. The surgical stapling device of claim 1, further including a biasing member, the biasing member being positioned to urge the slide member to a position to maintain the indicator in the first position.

14. The surgical stapling device of claim 13, wherein the biasing member is positioned about the proximal extension of the body of the slide member and is compressed between the housing of the handle assembly and the body of the slide member.

15. The surgical stapling device of claim 1, wherein the slide member includes a body portion defining an elongated slot, an upturned lip portion supporting a connector, and a proximal extension.

16. The surgical stapling device of claim 15, wherein the approximation mechanism includes a drive screw supporting a screw stop, the screw stop including a protrusion positioned within the elongated slot of the slide member, wherein movement of the drive screw to move the anvil assembly to the approximated position effects movement of the protrusion through the elongated slot into contact with the slide member, wherein contact of the protrusion with the slide member effects movement of the slide member to pivot the indicator from the first position to the second position.

* * * * *